(12) United States Patent
Crawley et al.

(10) Patent No.: US 12,378,173 B2
(45) Date of Patent: Aug. 5, 2025

(54) METHOD OF PRODUCTION OF BICYCLIC HYDROCARBONS

(71) Applicants: CleanJoule, Inc., Salt Lake City, UT (US); Matthew Raymond Crawley, Amherst, NY (US); Timothy Raymond Cook, Amherst, NY (US)

(72) Inventors: Matthew Raymond Crawley, Amherst, NY (US); Oyvind Hatlevik, West Valley City, UT (US); Robert Andrew Price, Salt Lake City, UT (US); Mukund Karanjikar, Salt Lake City, UT (US); Timothy Raymond Cook, Amherst, NY (US)

(73) Assignee: CleanJoule, Inc., Salt Lake City, UT (US)

( * ) Notice: Subject to any disclaimer, the term of this patent is extended or adjusted under 35 U.S.C. 154(b) by 0 days.

(21) Appl. No.: 18/986,289

(22) Filed: Dec. 18, 2024

(65) Prior Publication Data
US 2025/0197326 A1    Jun. 19, 2025

Related U.S. Application Data

(60) Provisional application No. 63/611,693, filed on Dec. 18, 2023.

(51) Int. Cl.
C07C 1/22     (2006.01)
C07C 13/605   (2006.01)
C10L 1/04     (2006.01)

(52) U.S. Cl.
CPC .............. C07C 13/605 (2013.01); C07C 1/22 (2013.01); C10L 1/04 (2013.01); *C07C 2603/62* (2017.05)

(58) Field of Classification Search
CPC ....... C07C 15/00; C07C 15/20; C07C 13/605; C07C 1/20; C07C 1/26; C07C 1/28; C07C 1/22; C07C 1/00
See application file for complete search history.

(56) References Cited

U.S. PATENT DOCUMENTS 2,925,445 A    2/1960   Bluestone
4,328,383 A    5/1982   Eschenmoser et al.
(Continued)

FOREIGN PATENT DOCUMENTS

CA    782623 A    4/1968
DE    1543228 A1  4/1969
DE    2513803 A1  10/1975

OTHER PUBLICATIONS

G.O. Ezinkwo et al "Overview of the Catalytic Production of Isoprene fromdifferent raw materials; Prospects of Isoprene productionfrom bio-ethanol." "Catalysis for Sustainable EnergyMinireview • DOI: 10.2478/cse-2013-0006 • CSE • 2013 • 100-111".

(Continued)

*Primary Examiner* — Sharon Pregler
(74) *Attorney, Agent, or Firm* — Caldwell Intellectual Property Law (57) ABSTRACT

A method for producing a bicyclic hydrocarbon molecule includes oxidizing a terpene molecule to provide a first intermediate compound, wherein the first intermediate compound includes an aldehyde functional group, reacting the first intermediate compound with a 1,3-diene molecule to form a second intermediate compound including the aldehyde functional group, and reducing the second intermediate compound to yield a first bicyclic hydrocarbon molecule, wherein reducing the second intermediate compound includes removing the aldehyde functional group.

18 Claims, 4 Drawing Sheets

(56) References Cited

U.S. PATENT DOCUMENTS

| | | | | |
|---|---|---|---|---|
| 8,715,486 B2* | 5/2014 | Myllyoja | ................... | C11C 1/04 |
| | | | | 208/66 |
| 2009/0076290 A1* | 3/2009 | Krasutsky | .............. | C07J 63/008 |
| | | | | 552/510 |

OTHER PUBLICATIONS

William N. Hunter "The Non-mevalonate Pathwayof Isoprenoid PrecursorBiosynthesis*" The Journal of Biological Chemistry vol. 282, No. 30, pp. 21573-21577, Jul. 27, 2007.

F. Kaplan et al "The Geometry of Myrtenal. A Detailed Analysis of the Nuclear MagneticResonance Spectrum of a Bicyclo[3.1. I] heptene-2 System" "The Journal of Organic Chemistryvol. 33, No. 5, May 1968".

Cjhi Ma et al "Synthesis and Performance of Strained Multicyclic Hydrocarbons asHighly Potential High-Energy-Density Fuels" Applied Chemistry Jul. 19, 2021.

Yanlong Qi et al."Synthesis of 1,3-Butadiene and Its 2-SubstitutedMonomers for Synthetic Rubbers" Catalysts 2019, 9, 97; doi: 10.3390/catal9010097.

Gabriel D. Roy "Utilization of High-Density StrainedHydrocarbon Fuels for Propulsion" "Journal of Propulsion and Powervol. 16, No. 4, Jul.-Aug. 2000".

P. O. Wennberg et al Gas-Phase Reactions of Isoprene and Its Major Oxidation Products Chemical Reviews 2018 118 (7), 3337-3390.

J D Woodroffe et al "Chemoselective Hydrogenation of Ring-StrainedMonoterpenes: A Route to High-PerformanceSustainable Aviation Fuels" Energy Technol. 2021, 9, 2100221.

* cited by examiner

METHOD OF PRODUCTION OF BICYCLIC HYDROCARBONS

CROSS-REFERENCE TO RELATED APPLICATIONS

This application claims the benefit of priority of U.S. Provisional Application Ser. No. 63/611,693, filed on Dec. 18, 2023, and entitled "METHOD FOR PRODUCTION OF BICYCLIC HYDROCARBON", the entirety of which is incorporated herein by reference.

STATEMENT OF GOVERNMENT SUPPORT

This invention was made with government support under WBI-IL-2020-02-002, awarded by the United States Department of Defense. The government has certain rights in the invention.

FIELD OF THE INVENTION

The present invention generally relates to the field of organic synthesis. In particular, the present invention is directed towards a method of production of bicyclic hydrocarbons.

BACKGROUND

The use of highly strained hydrocarbons has garnered increased attention in recent decades as potential fuel sources. The use of such highly strained hydrocarbons, including without limitation cyclic alkanes, holds potential in volume-limited applications found in military and civilian aerospace technologies. These highly strained hydrocarbons often have a superior energy density, which provides for a higher volumetric net het of combustion (NHOC) and potentially enables longer endurance and greater range in aviation applications.

However, typical fuel sources (i.e., petroleum sources) are usually devoid of such highly strained chemical species; therefore, these chemical species are primarily produced via chemical synthesis instead of distillation and purification of petroleum products. However, existing synthetic tools for highly strained hydrocarbons are often plagued by low reaction yields, competing side reactions, and/or the like, as the distorted bond angles, contorted geometries, and/or strong steric effects within these hydrocarbons often render them chemically unstable and energetically unfavored.

Terpenes are natural products of high bioavailability that often feature complex and strained structures. However, reliable strategies of using terpenes as feedstocks to produce highly strained hydrocarbons do not yet exist.

SUMMARY OF THE DISCLOSURE

In an aspect, a method for producing a bicyclic hydrocarbon molecule is described. The method includes oxidizing a terpene molecule to provide a first intermediate compound, wherein the first intermediate compound includes an aldehyde functional group. The method further includes reacting the first intermediate compound with a 1,3-diene molecule to form a second intermediate compound including the aldehyde functional group. The method further includes reducing the second intermediate compound to yield a first bicyclic hydrocarbon molecule, wherein reducing the second intermediate compound includes removing the aldehyde functional group. In one or more embodiments, the method may further include hydrogenating the first bicyclic hydrocarbon molecule to produce a second bicyclic hydrocarbon molecule.

In one or more embodiments, the terpene molecule may include a monoterpene with a chemical formula of $C_{10}H_{16}$. In some cases, the monoterpene may include a pinene such as without limitation α-pinene.

In one or more embodiments, the terpene molecule may be oxidized using selenium dioxide ($SeO_2$) as an oxidizing agent. In one or more embodiments, the oxidation of the terpene molecule may be performed using ethanol (EtOH) as a solvent. In one or more embodiments, the first intermediate compound may include myrtenal.

In one or more embodiments, the reaction between the first intermediate compound and the 1,3-diene molecule may include a Diels-Alder reaction or a [4+2] cycloaddition reaction. In one or more embodiments, the 1,3-diene molecule may include isoprene. In one or more embodiments, the reaction between the first intermediate compound and the 1,3-diene molecule may be catalyzed by a catalyst. In some cases, the catalyst may include a Lewis acid. In some cases, the catalyst may include a concentration of boron trifluoride dissolved in diethyl ether. In some cases, the catalyst may include $BF_3 \cdot Et_2O$.

In one or more embodiments, the second intermediate compound may have a chemical structure of I as shown below:

(I)

In one or more embodiments, the second intermediate compound may be reduced using a reducing agent, wherein the reducing agent includes hydrazine monohydrate or $N_2H_4 \cdot H_2O$.

In some cases, the reducing agent may be dispersed in an ethylene glycol solution having a concentration of potassium hydroxide (KOH).

In one or more embodiments, the first bicyclic hydrocarbon molecule may include a sesquiterpene molecule or a $C_{15}$ terpenoid molecule.

In one or more embodiments, the first bicyclic hydrocarbon molecule may have a chemical formula of $C_{15}H_{24}$.

In one or more embodiments, the first bicyclic hydrocarbon molecule may include an unsaturated bicyclic hydrocarbon molecule having at least one double bond, such as without limitation at least one carbon-carbon double bond.

In one or more embodiments, the first bicyclic hydrocarbon molecule may include a trimethylbicyclo[4.4.0]-7-decene. In some cases, the first bicyclic hydrocarbon molecule or trimethylbicyclo[4.4.0]-7-decene may include 2,2,7-trimethyl-1,3-methylenebicyclo[4.4.0]-7-decene. In some cases, the first bicyclic hydrocarbon molecule or trimethylbicyclo[4.4.0]-7-decene may have a chemical structure II as shown below:

(II)

In one or more embodiments, the first bicyclic hydrocarbon molecule may be hydrogenated using a hydrogenation catalyst. In some cases, the hydrogenation catalyst may include a Crabtree's catalyst, Raney nickel, or palladium (IV) oxide ($PdO_2$), among others.

In one or more embodiments, the second bicyclic hydrocarbon molecule may have a chemical formula of $C_{15}H_{26}$.

In one or more embodiments, the second bicyclic hydrocarbon may include a trimethylbicyclo[4.4.0]decane. In some cases, the second bicyclic hydrocarbon molecule or trimethylbicyclo[4.4.0]decane may include 2,2,7-trimethyl-1,3-methylenebicyclo[4.4.0]decane. In some cases, the second bicyclic hydrocarbon molecule or trimethylbicyclo[4.4.0]decane may have a chemical structure III as shown below:

(III)

In another aspect, a bicyclic hydrocarbon fuel molecule is described. The bicyclic hydrocarbon fuel molecule has a chemical structure of III, consistent with details described above:

(III)

In another aspect, a composition of matter for use as a fuel is described. The composition includes a bicyclic hydrocarbon fuel molecule having a chemical structure of III, consistent with details described above:

(III)

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3 is a set of three NMR spectra of (from top to bottom) THN-aldehyde, a nonlimiting example of the second intermediate molecule described in FIG. 1; (1S,3R,8aR)-2,2,6,8a-tetramethyl-1,2,3,4,4a,5,8,8a-octahydro-1,3-methanonaphthalene (hereinafter "THN-olefin"), a nonlimiting example of the first bicyclic compound described in FIG. 1; and (1S,3R,8aR)-2,2,6,8a-tetramethyl-decahydro-1,3-methanonaphthalene (hereinafter "hydro-THN"), a nonlimiting example of the second bicyclic compound described in FIG. 1; all spectra were acquired on a spectrometer operating at 500 MHz in deuterated chloroform ($CDCl_3$); the chemical shift scale is broken to highlight the aldehyde, olefin, and aliphatic regions; the dashed lines correlate the peaks that correspond to the same proton(s) throughout the reaction sequence.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a method of producing a bicyclic hydrocarbon molecule. Specifically, aspects of the present disclosure pertain to an alternative Diels-Alder reaction followed by hydrogenation to afford a desired sesquiterpene ($C_{15}$ hydrocarbon) product.

Aspects of the present disclosure may provide new synthetic strategies for highly strained organic molecules. Aspects of the present disclosure may expand the applicable scope of Diels Alder reactions in organic synthesis. Aspects of the present disclosure can be used to produce novel aviation fuels with a superior energy density. Exemplary embodiments illustrating aspects of the present disclosure are described below in the context of several specific examples.

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

It is to be understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (e.g., a step is performed by or with the assistance of a human).

For the purposes of this disclosure, including the claims, the phrase "at least some" means "one or more" and includes the case of only one. Thus, e.g., the phrase "at least some ABCs" means "one or more ABCs" and includes the case of only one ABC.

For the purposes of this disclosure, including the claims, the term "at least one" should be understood as meaning "one or more" and therefore includes both embodiments that include one or multiple components. Furthermore, dependent claims that refer to independent claims that describe features with "at least one" have the same meaning, both when the feature is referred to as "the" and "the at least one".

For the purposes of this disclosure, the term "portion" means some or all. Therefore, for example, "A portion of X" may include some of "X" or all of "X". In the context of a conversation, the term "portion" means some or all of the conversation.

For the purposes of this disclosure, including the claims, the phrase "using" means "using at least" and is not exclusive. Thus, e.g., the phrase "using X" means "using at least X". Unless specifically stated by use of the word "only", the phrase "using X" does not mean "using only X".

For the purposes of this disclosure, including the claims, the phrase "based on" means "based in part on" or "based, at least in part, on" and is not exclusive. Thus, e.g., the phrase "based on factor X" means "based in part on factor X" or "based, at least in part, on factor X". Unless specifically stated by use of the word "only", the phrase "based on X" does not mean "based only on X".

In general, for the purposes of this disclosure, including the claims, unless the word "only" is specifically used in a phrase, it should not be read into that phrase.

For the purposes of this disclosure, including the claims, the phrase "distinct" means "at least partially distinct". Unless specifically stated, distinct does not mean fully distinct. Thus, e.g., the phrase "X is distinct from Y" means that "X is at least partially distinct from Y" and does not mean that "X is fully distinct from Y". Thus, for the purposes of this disclosure, including the claims, the phrase "X is distinct from Y" means that X differs from Y in at least some way.

It should be appreciated that the words "first", "second", and so on, in the description and claims, are used to distinguish or identify, and not to show a serial or numerical limitation.

Similarly, letter labels (e.g., "(A)", "(B)", "(C)", and so on, or "(a)", "(b)", and so on) and/or numbers (e.g., "(i)", "(ii)", and so on) are used to assist in readability and to help distinguish or identify, and are not intended to be otherwise limiting or to impose or imply any serial or numerical limitations or orderings. Similarly, words such as "particular", "specific", "certain", and "given", in the description and claims, if used, are to distinguish or identify, and are not intended to be otherwise limiting.

For the purposes of this disclosure, including the claims, the terms "multiple" and "plurality" mean "two or more," and include the case of "two". Thus, e.g., the phrase "multiple ABCs" means "two or more ABCs" and includes "two ABCs". Similarly, e.g., the phrase "multiple PQRs" means "two or more PQRs" and includes "two PQRs".

The present invention also covers the exact terms, features, values, and ranges, etc., in case these terms, features, values, and ranges, etc., are used in conjunction with terms such as "about", "around", "generally", "substantially", "essentially", "at least", etc. Thus, e.g., "about 3" or "approximately 3" shall also cover exactly 3, and "substantially constant" shall also cover exactly constant.

For the purposes of this disclosure, unless stated otherwise, the terms "about" or "approximately" refer to a value that is within 10% above or below the value being described.

For the purposes of this disclosure, including the claims, singular forms of terms are to be construed as also including the plural form and vice versa, unless the context indicates otherwise. Thus, it should be noted that for the purposes of this disclosure, the singular forms "a", "an", and "the" include plural references unless the context clearly dictates otherwise. In other words, terms such as "a", "an", and "the" are not intended to refer to only a singular entity but include the general class of which a specific example may be used for illustration.

Throughout the description and claims, the terms "comprise", "including", "having", "contain", and their variations should be understood as meaning "including but not limited to" and are not intended to exclude other components unless specifically so stated.

It will be appreciated that variations to the embodiments of the invention can be made while still falling within the scope of the invention. Alternative features serving the same, equivalent, or similar purpose can replace features disclosed in the specification, unless stated otherwise. Thus, unless stated otherwise, each feature disclosed represents one example of a generic series of equivalent or similar features.

Use of exemplary language, such as "for instance", "such as", "for example" ("e.g.,"), and the like, is merely intended to better illustrate the invention and does not indicate a limitation on the scope of the invention unless specifically so claimed.

While the invention has been described in connection with what is presently considered to be the most practical and embodiments thereof are further described in the examples below, it is to be understood that the invention is not to be limited to the disclosed embodiment, but on the contrary, is intended to cover various modifications and equivalent arrangements included within the spirit and scope of the appended claims.

The following description sets forth various examples along with specific details to provide a thorough understanding of the claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

It will be appreciated that embodiments disclosed herein may be employed in a variety of fields and/or operating environments where the functionality disclosed herein may be useful. Accordingly, the scope of the claims should not be construed to be limited to the exemplary implementations and operating environments disclosed herein.

Figure 1:
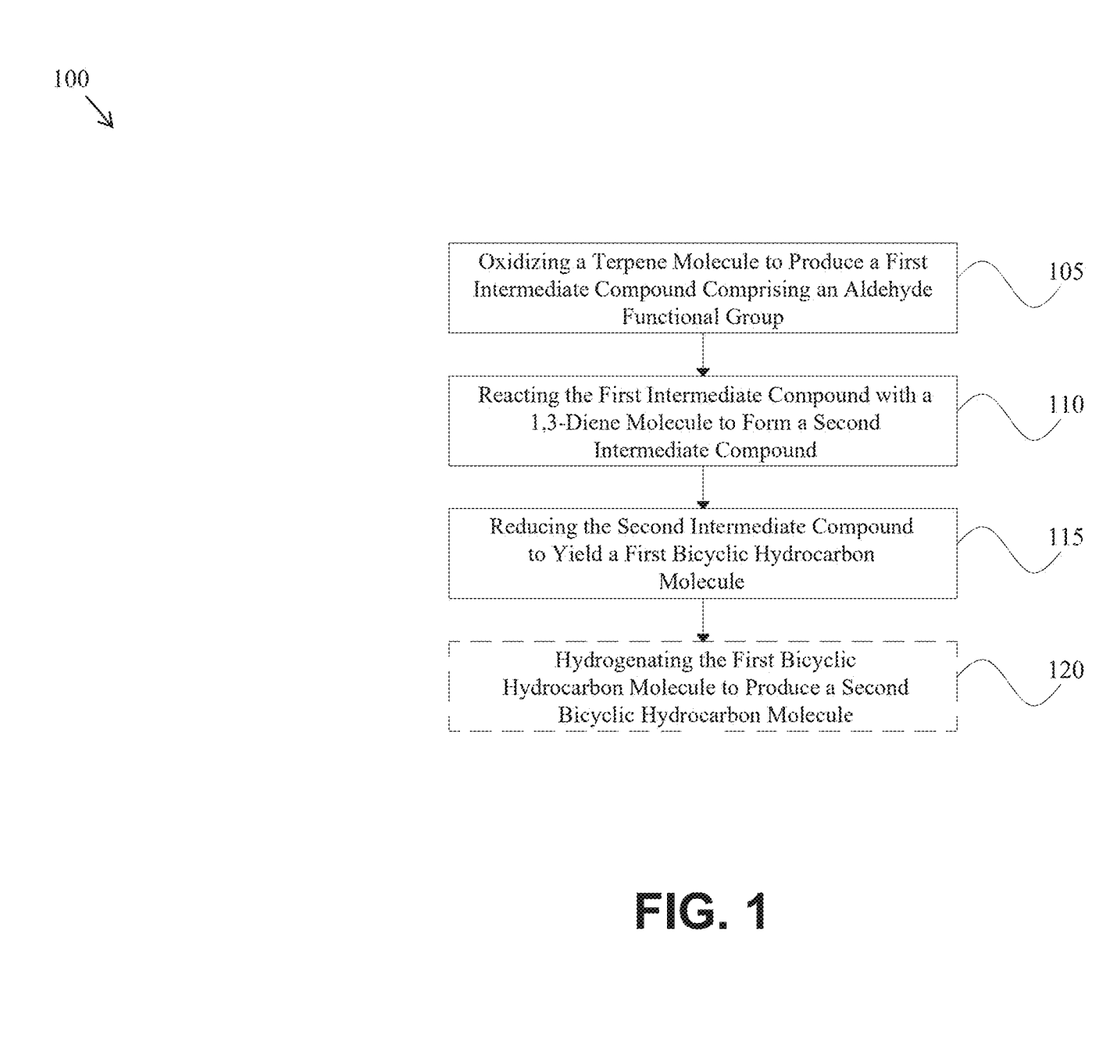
FIG. 1 is a schematic illustration of an exemplary embodiment of a method for producing bicyclic hydrocarbons.

Referring now to FIG. 1, an exemplary embodiment of a method 100 for producing a bicyclic hydrocarbon molecule is illustrated. At step 105, Method 100 includes oxidizing a terpene molecule to provide a first intermediate compound. In one or more embodiments, the terpene molecule may include a monoterpene with a chemical formula of $C_{10}H_{16}$. In some cases, the monoterpene may include a pinene, such as without limitation α-pinene. For the purposes of this disclosure, "α-pinene" is a bicyclic monoterpene hydrocarbon with the molecular formula $C_{10}H_{16}$, characterized by a fused cyclobutane and cyclohexene structure with a double bond in the six-membered ring. α-pinene has two enantiomers, i.e., (+)-α-pinene and (−)-α-pinene, which differ in the spatial arrangement of their substituents. α-pinene is a naturally occurring compound commonly derived from coniferous trees and certain plants, serving as a primary constituent of turpentine oil. α-pinene may be used in industrial applications such as without limitation as a precursor in the synthesis of fragrances, resins, and pharmaceuticals, as a solvent or intermediate in organic chemical processes, etc. For the purposes of this disclosure, a "pinene" is a bicyclic monoterpene hydrocarbon with the molecular formula $C_{10}H_{16}$. Pinene has two structural isomers, α-pinene (as described above) and β-pinene, which differ in the location of the double bond within the bicyclic framework. Both isomers exhibit a fused cyclobutane and cyclohexene ring system, with α-pinene featuring a double bond in the six-membered ring, as described above, and β-pinene featuring a double bond in the four-membered ring instead. Pinenes are naturally occurring compounds predominantly found in essential oils derived from coniferous trees and other plants. Pinene may serve as a key component in the production of fragrances, resins, and flavoring agents, as well as an intermediate in synthetic chemical processes, including without limitation the preparation of pharmaceutical and industrial compounds.

With continued reference to FIG. 1, for the purposes of this disclosure, a "terpene" is an organic compound with the general molecular formula $(C_5H_8)$ n, often characterized by a structure that contains repeating $C_5H_8$ units. Terpenes are produced predominantly by plants, particularly conifers, and certain insects, and may be involved in various biological functions, including defense mechanisms and communication. Terpenes may be classified as monoterpenes (n=2), sesquiterpenes (n=3, as described in further detail below), diterpenes (n=4), and higher terpenes (n>4), based on the number of isoprene units they contain. Monoterpenes ($C_{10}H_{16}$) may include without limitation limonene found in citrus peels, myrcene in hops and lemongrass, pinene in pine resin, linalool in lavender, and geraniol in rose oil, among others. Sesquiterpenes ($C_{15}H_{24}$) may include without limitation farnesene in apple coatings, humulene in hops, bisabolol in chamomile, caryophyllene in black pepper, and nerolidol in ginger and tea tree oil. Diterpenes ($C_{20}H_{32}$) may include without limitation taxadiene from yew trees, gibberellins as plant hormones, phytol in chlorophyll, steviol in Stevia leaves, and retinol (Vitamin A1) derived from β-carotene. Higher terpenes may include without limitation squalene ($C_{30}H_{50}$) in shark liver oil, lanosterol ($C_{30}H_{50O}$) in wool grease, tetraterpenes or tetraterpenoids including carotenoids ($C_{40}H_{56}$) such as beta-carotene in carrots, and rubber (polyterpene) from latex. Terpenes may serve as a biochemical precursor for a wide array of natural products, including essential oils, resins, and various pharmacologically active compounds, making them valuable in industries such as pharmaceuticals, perfumery, and agriculture. Terpenes belong to a broader class of molecules called terpenoids. A terpenoid may include a molecule that is derived from a terpene. Terpenoids include a large and diverse class of naturally occurring organic compounds and may play essential roles in various biological processes, including without limitation cellular membrane structure (as cholesterol), photosynthesis (as carotenoids), and growth regulation (as gibberellins). Terpenoids may also be used in pharmaceuticals, fragrances, and biofuels due to their diverse chemical properties and biological activities.

With continued reference to FIG. 1, in one or more embodiments, the terpene molecule may be oxidized using selenium dioxide ($SeO_2$) as an oxidizing agent. In one or more embodiments, the oxidation of the terpene molecule may be performed using ethanol (EtOH) as a solvent.

With continued reference to FIG. 1, the first intermediate compound includes an electron withdrawing functional group. For the purposes of this disclosure, an "electron-withdrawing functional group" or "electron-withdrawing group" is a single atom, a group of atoms, or a substituent within a chemical species that is capable of electrostatically attracting electron density towards itself and away from the rest of the chemical species. The chemical species described herein may include without limitation any organic molecules or ions. An electron-withdrawing group may include a single atom of a large electronegativity. Alternatively, an electron-withdrawing group may include a cluster of atoms, at least one of which has a large electronegativity. An electron-withdrawing group may include a halogen, i.e., a fluorine, chlorine, bromine, or iodine; a nitro group (—$NO_2$); a cyano group (—C≡N); a carbonyl-containing group such as without limitation an aldehyde (—CHO), a ketone (—CO—), a carboxyl group (—COOH), an ester group (—COOR), or an amide group (—$CONR_2$); a sulfonyl group (—$SO_2R$); a trifluoromethyl group (—$CF_3$); a perfluoroalkyl group (—$C_nF_{2n+1}$); and/or another highly electronegative functional group recognized by a person of ordinary skill in the art, upon reviewing the entirety of this disclosure. A functional group with a strong resonance effect, such as —$NO_2$, —C≡N, or a carbonyl-containing group, may have a particularly strong electron-withdrawing effect due to its ability to delocalize charge through conjugation. An electron-withdrawing group may have an impact on the reactivity and/or stability of a chemical species. As a nonlimiting example, an electron-withdrawing group may direct electrophilic aromatic substitution to a meta position as opposed to an ortho or para position. As another nonlimiting example, an electron-withdrawing group may increase the acidity (i.e., lower the $pK_a$) of an adjacent proton by polarizing a chemical bond such as without limitation an O—H bond. As another nonlimiting example, an electron-withdrawing group may increase the affinity of a dienophile towards a conjugated diene or the like and facilitate a Diels-Alder reaction, additional details of which will be provided below in this disclosure.

With continued reference to FIG. 1, in one or more embodiments, the first intermediate compound may include myrtenal. For the purposes of this disclosure, "myrtenal" is a naturally occurring monoterpene aldehyde, chemically represented as $C_{10}H_{14}O$, characterized by its bicyclic structure derived from pinene. Myrtenal includes a reactive aldehyde functional group and a conjugated double bond within its bicyclic framework, imparting unique chemical and biological properties. In some cases, myrtenal may be obtained through the oxidation of myrtenol or as a natural extract from certain plant species. Myrtenal is used as a precursor in the synthesis of fine chemicals, fragrances, and bioactive compounds. The biological properties of myrtenal, including without limitation antimicrobial, anti-inflammatory, and antioxidant activities, among others, make it a valuable component in formulations for therapeutic and cosmetic products. The chemical versatility of myrtenal makes it a useful building block in synthetic chemistry to produce value-added products across various industrial domains. The chemical structure of myrtenal may be found in Scheme 1 below in this disclosure.

With continued reference to FIG. 1, at step 110, method 100 further includes reacting the first intermediate compound with a 1,3-diene molecule or the like to form a second intermediate compound. The second intermediate compound retains electron-withdrawing group (e.g., the aldehyde functional group) described above in order to increase its reactivity in subsequent steps.

With continued reference to FIG. 1, in one or more embodiments, the reaction between the first intermediate compound and the 1,3-diene molecule may include a Diels-Alder reaction or a [4+2] cycloaddition reaction. For the purposes of this disclosure, a "Diels-Alder reaction" or a "[4+2] cycloaddition reaction" is a chemical reaction between a conjugated diene with four π-electrons and a dienophile with two conjugated π-electrons that forms a six-membered cyclic compound. A Diels-Alder reaction proceeds through a concerted mechanism that involves the simultaneous reorganization of bonding electrons. A Diels-Alder reaction is characterized by its high regioselectivity and stereospecificity, enabling precise control over the formation of complex cyclic structures. It is widely utilized in the synthesis of biologically active compounds, polymers, and materials, as well as in the preparation of intermediates for pharmaceuticals, agrochemicals, and fine chemicals. The versatility in constructing diverse molecular frameworks, including heterocycles and fused-ring systems, makes Diels-Alder reactions a foundational method in synthetic organic chemistry. For the purpose of this disclosure, a "dienophile" is a chemical species, often an unsaturated molecule, that has an affinity towards dienes. In some cases, a Diels-Alder reaction may occur under thermal conditions without requiring a catalyst. In some cases, a Diels-Alder reaction may be catalyzed by a catalyst, as described in further below in this disclosure.

With continued reference to FIG. 1, for the purposes of this disclosure, "catalysis" is a process wherein a chemical species accelerates a chemical reaction by lowering at least an activation barrier along a reaction coordinate and increases at least a rate constant associated with the at least an activation barrier. The chemical species capable of performing catalysis is accordingly classified as a catalyst. In some cases, to perform a catalytic function, a catalyst may first be consumed by one or more reactants to form one or more intermediates, then be regenerated as the one or more intermediates are converted to one or more products. In other words, a catalyst may not be consumed as a net result and accordingly may not be included as a reactant in a net chemical reaction. The catalytic function or activity of a catalyst may be described using mathematical tools such as Arrhenius equation, Eyring equation. Michaelis-Menten equation, Lineweaver-Burk equation, among others, as deemed suitable by a person of ordinary skill in the art upon reviewing the entirety of this disclosure.

With continued reference to FIG. 1, in one or more embodiments, the 1,3-diene molecule may include isoprene. For the purposes of this disclosure, "isoprene", also known as 2-methyl-1,3-butadiene, is a volatile organic compound with the chemical formula $C_5H_8$, a structural formula of $CH_2$=$CHC(CH_3)$=$CH_2$, and a normal boiling point of 34° C. Isoprene may be considered a "hemiterpene" (i.e., half of a terpene), and the details of terpenes has been described above in this disclosure. Isoprene belongs to a broader class of molecules called isoprenoids, and the terms "isoprenoid" and "terpenoid" may be used interchangeably. Isoprene is a key building block for synthesizing natural rubber and various other polymers. Additionally, isoprene may be used in the manufacture of synthetic rubber, adhesives, and elastomers, as well as in the production of pharmaceuticals and other specialty chemicals. Isoprene may be produced naturally by plants and trees, particularly in large amounts by the rubber tree (i.e., *Hevea brasiliensis*). Isoprene may be produced through biotechnological methods, such as without limitation by using genetically engineered microbes. There have been growing efforts to access isoprene and other isoprenoids sustainably via extraction/production from biosynthesis. Current models suggest that biogenic isoprene emission releases approximately 500 Tg annually. As such, with improved sequestration and isolation techniques, access to sustainable low-cost isoprene may likely increase. Furthermore, feedstock production may further be secured through biosynthetic approaches. In addition, terpenes often feature complex and strained structures. This feature, in conjunction with their high bioavailability, makes terpenes suitable feedstocks for producing high-energy density hydrocarbons. Additional details will be provided below in this disclosure.

With continued reference to FIG. 1, additionally, and/or alternatively, isoprene may be synthesized using industrial organic chemistry, via synthetic routes such as an acetone/acetylene route, a propylene dimer route, an isoamylene route, an isopentane route, or an isobutylene/formaldehyde route, among others. Additionally, and/or alternatively, in some cases, isoprene may be produced via synthetic routes including without limitation dehydration of isopentane, synthesis from isobutylene and formaldehyde, liquid-phase oxidation of hydrocarbons, and/or the like. Additionally, and/or alternatively, in some cases, isoprene may be produced as a byproduct of liquid petroleum pyrolysis, such as without limitation by thermally cracking petroleum-derived naphtha.

With continued reference to FIG. 1, in one or more embodiments, the reaction between the first intermediate compound and the 1,3-diene molecule may be catalyzed by a catalyst. In some cases, the catalyst may include a Lewis acid catalyst. For the purposes of this disclosure, a "Lewis acid" is a chemical species that is capable of accepting an electron pair. In contrast, a chemical species that is capable of donating an electron pair is referred to as a Lewis base instead. A Lewis acid typically contains an atom without a complete octet within its valence electron shell. A Lewis acid often contains one or more moieties that are positively charged and/or associated with a positive oxidation number. Nonlimiting examples of Lewis acids may include without limitation metal cations (e.g., $Al^{3+}$, $Fe^{3+}$), halides of Group IIIA elements (e.g., $AlCl_3$, $BF_3$), and certain molecular compounds or species containing electron-deficient atoms (e.g., $SO_3$). Due to their often electron-deficient nature, Lewis acids are capable of coordinating with other chemical moieties and function as a catalyst. Specifically, Lewis acids may be used to activate one or more reactants by coordinating to lone pair(s) of one or more electronegative atoms (e.g., O, N, and/or the like) therein. Such interaction may reduce the electron density of the substrate, making it more reactive and prone to chemical transformations. Lewis acids may be used in catalytic processes including without limitation Friedel-Crafts alkylation and acylation, Diels-Alder reactions (as described above), epoxide opening reactions, and/or the like. The ability of Lewis acids in enhancing reaction rates and/or selectivity makes them a useful tool in synthetic organic chemistry and industrial processes. In some cases, the catalyst/Lewis acid catalyst may include a concentration of boron trifluoride dissolved in diethyl ether ($Et_2O$). In some cases, the catalyst/Lewis acid catalyst may include $BF_3 \cdot Et_2O$, which is a coordination complex between $BF_3$, a Lewis acid, and $Et_2O$, a Lewis base, in 1:1 stoichiometry.

With continued reference to FIG. 1, in one or more embodiments, the second intermediate compound may have a chemical structure of I as shown below:

(I)

With continued reference to FIG. 1, at step 115, method 100 further includes reducing the second intermediate compound to yield a first bicyclic hydrocarbon molecule. Specifically, reduction of the second intermediate compound includes removing the aldehyde functional group. In one or more embodiments, the second intermediate compound may be reduced using a reducing agent that includes hydrazine monohydrate or $N_2H_4 \cdot H_2O$. Specifically, through such a reduction step, the aldehyde group within the second intermediate compound may be converted to a methyl group, as shown in further detail below in Scheme 1. In some cases, the reducing agent may be dispersed in an ethylene glycol solution having a concentration of potassium hydroxide (KOH).

With continued reference to FIG. 1, for the purposes of this disclosure, "hydrazine monohydrate" is a chemical compound with the molecular formula $N_2H_4 \cdot H_2O$, consisting of hydrazine, $N_2H_4$, coordinated with a single water molecule, $H_2O$. Hydrazine monohydrate appears as a colorless, fuming liquid with a strong ammonia-like odor and is highly reactive due to its reducing properties and high nitrogen content. Hydrazine monohydrate may be applied in various chemical and industrial applications due to its versatility and ability to donate electrons in redox reactions. As nonlimiting examples, hydrazine monohydrate may be employed as a reducing agent in organic synthesis to reduce carbonyl compounds, nitro groups, and/or azides, among others. The ability of hydrazine monohydrate to decompose into nitrogen gas and water makes it a clean reducing agent with minimal byproducts.

With continued reference to FIG. 1, In one or more embodiments, the first bicyclic hydrocarbon molecule may have a chemical formula of $C_{15}H_{24}$. In one or more embodiments, the first bicyclic hydrocarbon molecule may include a sesquiterpene molecule or a $C_{15}$ terpenoid molecule. For the purposes of this disclosure, "sesquiterpene" molecules are a class of naturally occurring terpenes and/or terpenoids with three isoprene units. In general, a sesquiterpene has a molecular formula of $C_{15}H_{24}$ and may exist in various structural forms, including without limitation linear, monocyclic, bicyclic, and/or tricyclic frameworks, among others. Similar to discussions above pertaining to isoprenoids and terpenoids, it is worth noting that sesquiterpenes may not include hydrocarbons only and may instead incorporate one or more functional groups, including without limitation alcohols, ketones, aldehydes, acids (e.g., carboxyl), and/or the like. These factors may further add to the chemical and biological versatility of sesquiterpenes. Naturally occurring sesquiterpenes may be found in plants, fungi, and marine organisms, among others, often serving as key components of essential oils and other natural products. Sesquiterpenes may have nontrivial utility in pharmaceutical, cosmetic, and industrial applications due to their bioactive properties, such as antimicrobial, anti-inflammatory, and/or antioxidant activities. Additionally, sesquiterpenes may be used as a versatile building block for synthesizing fine chemicals, fragrances, therapeutic agents, and/or the like.

With continued reference to FIG. 1, in one or more embodiments, the first bicyclic hydrocarbon molecule may include an unsaturated bicyclic hydrocarbon molecule having at least one double bond, such as without limitation one carbon-carbon double bond.

With continued reference to FIG. 1, in one or more embodiments, the first bicyclic hydrocarbon molecule may include a trimethylbicyclo[4.4.0]-7-decene. In some cases, the first bicyclic hydrocarbon molecule or trimethylbicyclo[4.4.0]-7-decene may include 2,2,7-trimethyl-1,3-methylenebicyclo[4.4.0]-7-decene. In some cases, the first bicyclic hydrocarbon molecule or trimethylbicyclo[4.4.0]-7-decene may have a chemical structure II as shown below:

(II)

With continued reference to FIG. 1, in one or more embodiments, at step 120, method 100 further includes hydrogenating the first bicyclic hydrocarbon molecule to produce a second bicyclic hydrocarbon molecule. For the purposes of this disclosure, "hydrogenation" is a type of chemical reaction wherein a plurality of hydrogen atoms is added across an unsaturated chemical bond in a molecule or ion, thereby increasing the degree of saturation in the molecule or ion. The unsaturated chemical bond may include a double bond such as a C═C bond or a triple bond such as a C≡C bond.

With continued reference to FIG. 1, in one or more embodiments, the first bicyclic hydrocarbon molecule may be hydrogenated using a hydrogenation catalyst. For the purposes of this disclosure, a "hydrogenation catalyst" is a chemical species or chemical composition that is capable of catalyzing a hydrogenation reaction. In some cases, the hydrogenation catalyst may include without limitation a Crabtree's catalyst (i.e., $[C_8H_{12}IrP(C_6H_{11})_3C_5H_5N]PF_6$), an iron (Fe)-based catalyst, a magnesium (Mg)-based catalyst, a ruthenium (Ru)-based catalyst, an aluminum (Al)-based catalyst, a nickel (Ni)-based catalyst including a rhenium-nickel (Re—Ni) alloy, a nickel-aluminum (Ni—Al) alloy, Raney nickel, Ni supported on silica-alumina ($SiO_2$—$Al_2O_3$), among others, a chromium (Cr)-based catalyst, a platinum (Pt)-based catalyst including platinum (IV) oxide ($PtO_2$) (which is also known as platinum (IV) oxide hydrate, $PtO_2 \cdot H_2O$, platinum dioxide, or Adam's catalyst), and/or a palladium (Pd)-based catalyst including Pd black, Pd supported on carbon (Pd/C), Pd supported on $CaCO_3$ (Pd/$CaCO_3$), Pd supported on $BaSO_4$ (Pd/$BaSO_4$), Pd supported on $SiO_2$ (Pd/$SiO_2$), and Pd supported on $CaCO_3$ (Pd/$Al_2O_3$), among others. Details described herein pertaining to hydrogenation may be consistent with any detail disclosed in U.S.

patent application Ser. No. 18/928,691, filed on Oct. 28, 2024, entitled "SYSTEMS AND METHODS FOR PRODUCING A DIMETHYLCYCLOOCTANE-BASED AVIATION FUEL FROM ISOPRENE", the entirety of which is incorporated herein by reference. A person of ordinary skill in the art, upon reviewing the entirety of this disclosure, will be able to recognize proper means to implement a hydrogenation catalyst for step 120 in method 100.

With continued reference to FIG. 1, in one or more embodiments, the second bicyclic hydrocarbon molecule may have a chemical formula of $C_{15}H_{26}$. In one or more embodiments, the second bicyclic hydrocarbon may include a trimethylbicyclo[4.4.0]decane. In some cases, the second bicyclic hydrocarbon molecule or trimethylbicyclo[4.4.0] decane may include 2,2,7-trimethyl-1,3-methylenebicyclo [4.4.0]decane. In some cases, the second bicyclic hydrocarbon molecule or trimethylbicyclo[4.4.0]decane may have a chemical structure III as shown below:

(III)

With continued reference to FIG. 1, the bicyclic hydrocarbon fuel molecule with structure III may be used as a fuel, either by itself or in combination with other chemical species as a composition of matter, formulation, or fuel blend. A nonlimiting example of the overall synthetic strategy outlined in method 100 is summarized below as Scheme 1.

Scheme 1: Synthetic Strategy for a Bicyclic Hydrocarbon.

Examples

The following examples are intended to be illustrative of the disclosure only and are not intended to limit the scope or underlying principles in any way. The examples specifically describe a new ring-strained polycyclic alkane and a method of manufacture thereof using non-petroleum-based feedstocks. A range of spectroscopic techniques were used to structurally characterize the resulting polycyclic alkane. An analysis of gravimetric and volumetric net het of combustion (NHOC) reveals that this ring-strained polycyclic alkane meets or exceeds both Jet-A and JP-10 requirements. This work demonstrates the potential use of polycyclic alkanes as next-generation fuel sources in both military and civilian applications.

Synthesis of THN-Aldehyde (a Nonlimiting Example of the Second Intermediate Compound)

50.0 mL (0.329 mol) of myrtenal was added to a 5-L two-neck flask under an $N_2$ atmosphere and dissolved in 2.0 L of diethyl ether. A magnetic stir bar was added to the mixture, and the solution was rapidly stirred upon addition of 350 mL (3.50 mol) of isoprene. The reaction mixture was cooled to 0° C., and 50.0 mL (0.306 mol) of $BF_3 \cdot EtO_2$ was added dropwise to the reaction mixture. The reaction mixture was then warmed to room temperature and stirred for 3 days to form an orange reaction mixture. The mixture was quenched by adding 1.0 L of water and stirred for 30 mins. The organic layer was collected and extracted with 500 mL of water. The aqueous layer was extracted with 3×100 mL of diethyl ether. The organic fractions were combined, and diethyl ether was removed by rotary evaporation until a constant volume was reached as a brown oil. The oil was diluted with one volume equivalent of hexanes and placed in the freezer overnight. The product crystallized as large, clear, colorless crystals, which were collected by vacuum filtration and washed with cold (−20° C.) hexanes. Yield: 73.7% (53.2 g, 0.244 mol). Note, this isolation may work at larger scales (i.e., to yield >1 gram of the brown oil). When ran on a smaller scale, column chromatography may be used instead to purify the product ($SiO_2$, mobile phase: 9:1 hexanes to ether); THN-aldehyde was the first band to elute. TLC: $R_f$ of 0.6 in 9:1 hexanes to ether. $^1H$ NMR ($CDCl_3$, 500 MHz): δ 9.34 ($1H_{aldehdye}$, S), 5.34 ($1H_{olefin}$, s), 2.57 (1H, dddd, J=11.3, 10.0, 6.4, 3.6 Hz), 2.32-2.20 (3H, m), 2.14 (1H, dd, J=6.3, 5.1, Hz), 2.02 (1H, m), 1.95-1.84 (2H, m), 1.82-1.73 (1H, m), 1.76-1.71 ($3H_{methyl}$, s), 1.46 (1H, dt, J=13.5, 3.5 Hz), 1.32 (1H, d, J=10.4 Hz), 1.21 ($3H_{methyl}$, s), 0.66 ($3H_{methyl}$, s); $^{13}C$ $\{^1H\}$ NMR ($CDCl_3$, 126 MHz) δ 206.78, 139.80, 118.24, 55.85, 48.93, 41.14, 39.98, 39.65, 34.08, 30.13, 27.08, 26.66, 26.47, 23.13, 22.75. EI-MS: m/z $[M]^+$218 (calculated 218.17). FTIR (neat, $cm^{-1}$) 3052 (=C—H stretch), 2903 (aliphatic C—H stretch), 2860 and 2710 (aldehyde C—H stretch), 1722 (C=O stretch).

Synthesis of (1S,3R,8aS)-2,2,6,7-tetramethyl-2,3,4,4a,5,8-hexahydro-1,3-methanonaphthalene-8a (1H)-carbaldehyde (Hereinafter "THN-Aldehyde-Me") (a Nonlimiting Example of the Second Intermediate Compound)

The synthesis of THN-aldehyde-Me was analogous to that of THN-aldehyde; however, even in the freezer after purification, no crystallization occurred. Therefore, purification was performed using column chromatography instead, under the exact same conditions as THN-aldehyde. TLC: $R_f$ of 0.6 in 9:1 hexanes to ether. $^1$H NMR (CDCl$_3$, 500 MHz): δ 9.37 (1H$_{aldehyde}$, s), 2.51 (1H, m), 2.29-2.08 (5H, m), 1.89-1.76 (2H, m), 1.73 (1H, d, J=15 Hz), 1.68 (3H$_{methyl}$, s), 1.57 (3H$_{methyl}$, s), 1.46-1.39 (1H, m), 1.28 (1H, d, J=10 Hz), 1.20 (3H$_{methyl}$, s), 0.65 (3H$_{methyl}$, s). $^{13}$C {$^1$H} NMR (CDCl$_3$, 75.4 MHZ) § 207.05, 129.94, 124.48, 56.33, 49.06, 42.92, 40.24, 39.78, 37.03, 33.97, 27.14, 27.05, 26.75, 23.37, 19.05, 18.81.

Synthesis of THN-Olefin (a Nonlimiting Example of the First Bicyclic Hydrocarbon Molecule)

20.0 grams (0.0917 mol) of THN-aldehyde, 12.8 mL (13.2 g, 0.264 mol) of hydrazine monohydrate, and 125 mL of triethylene glycol were added to a 250-mL 3-neck flask. A water-cooled reflux condenser and two septa were fitted to the flask, and the reaction mixture was brought to reflux for 30 mins to convert the aldehyde group of THN-aldehyde to its corresponding hydrazone in situ. Afterwards, the two septa were removed, and 18.8 grams (0.335 mol) of pulverized KOH pellets were added slowly. It should be emphasized that this step should be performed slowly and in a well-ventilated reaction vessel, as KOH leads to the decomposition of the hydrazone to evolve N$_2$ gas. The reaction was then allowed to reflux for an additional 1.5 hours. The water-cooled condenser was then removed and replaced with a short-path distillation head. Water began distilling over at 100° C. After 1 hour, the collection bulb contained a biphasic mixture, the organic layer of which was collected and added back to the distillation flask. The contents of the distillation flask were extracted with petroleum ether. The aqueous layer was then neutralized with HCl (2.4 M) and extracted twice more with petroleum ether. The petroleum ether was removed by rotary evaporation to form a colorless, clear oil, which was further distilled under reduced pressure (65 millitorr), THN-olefin was collected at 75-77° C. as a colorless clear oil. Yield: 98.4% (18.4 grams, 0.0902 mol). $^1$H NMR (CDCl$_3$, 500 MHz): δ 5.63 (1H$_{olefin}$, s), 2.19-2.07 (2H, m), 2.07-2.00 (1H, m), 2.00-1.85 (2H, m), 1.81-1.71 (4H, m), 1.70-1.64 (1H, m), 1.61 (1H, t, J=5.0 Hz), 1.53 (1H, d, J=15.0 Hz), 1.29-1.19 (5H, m), 1.06 (3H$_{methyl}$, s), 0.97 (3H$_{methyl}$, s). $^{13}$C {$^1$H} NMR (CDCl$_3$, 125.7 MHz) δ 135.55, 123.33, 55.70, 40.96, 40.18, 40.02, 39.05, 37.64, 35.67, 35.07, 30.91, 28.40, 28.21, 23.98, 23.94. EI-MS: m/z [M]$^+$ 204 (calculated 204.19). FTIR (neat, cm$^{-1}$) 2911 (—C—H stretch), 1446, 1373, 796.

Synthesis of Hydro-THIN (a Nonlimiting Example of the Second Bicyclic Hydrocarbon Molecule)

THL-olefin is hydrogenated with higher pressure hydrogen in presence of Raney Ni catalyst to saturate the double bond. $^1$H NMR (CDCl$_3$, 500 MHz): δ 2.31-2.22 (1H, m) 2.21-2.14 (1H, m) 2.00-1.92 (1H, m), 1.91-1.83 (1H, m), 1.80-1.70 (1H, m), 1.59 (1H, dd, J=5.9 Hz, 5.9 Hz), 1.54-1.47 (1H, m), 1.47-1.41 (1H, m), 1.41-1.31 (1H, m), 1.31-1.25 (5H, m), 1.24-1.20 (1H, m), 1.17 (3H$_{methyl}$, s), 1.18-1.15 (4H, m), 1.05-1.02 (1H, m), 0.89 (3H$_{methyl}$, d, J=5.8 Hz). $^{13}$C {$^1$H} NMR (CDCl$_3$, 126 MHZ) § 55.76, 42.15, 39.58, 38.01, 36.81, 36.43, 35.87, 33.75, 32.26, 31.42, 29.85, 28.94, 27.41, 24.45, 22.87. EI-MS: m/z [M]$^+$206.211 (calculated 206.203). FTIR (neat, cm$^{-1}$) 2948 (—C—H stretch), 2897, 1456, 1367, 1230.

Synthesis and Discussion

Initial efforts focused on a direct Diels-Alder reaction between α-pinene and isoprene using a Lewis acid as a catalyst. This approach proved fruitless, owing to the lack of a polarizing functional group on the dienophile. Based on GC-MS data, the primary products were oligomers of isoprene and α-pinene. To facilitate the [4+2] cycloaddition, an electron withdrawing aldehyde group was installed at the allylic methyl group of α-pinene. This functionalization step may be performed by a Riley oxidation with SeO$_2$ to convert α-pinene to myrtenal. Treating myrtenal with isoprene using BF$_3$·Et$_2$O as a catalyst produced THN-aldehyde. The crude product was recrystallized from cold hexanes to form the product as a white crystalline solid which melted after prolonged periods at room temperature. THN-aldehyde was stable in the freezer at −20° C. for at least one year; however, after approximately 3 months at room temperature, some decomposition was observable by NMR spectroscopy. The analogous Diels-Alder reaction was performed with different dienes. Notably, the cyclization would only proceed when acyclic dienes were used. Attempts to cyclize with cyclopentadiene, anthracene, and 1,3-cyclohexadiene proved fruitless; however, when 2,3-dimethyl-1,3-butadiene was used, the reaction readily proceeded to products (THN-aldehyde-Me). This result has been attributed to a steric hinderance between the bridgehead carbon/protons of the α-pinene with the carbon atom(s) of the respective cyclic systems. The steric bulk hampers the approach of the diene to the dienophile and inhibits effective orbital overlap. To remove the aldehyde functionality, a Huang Minlon modified Wolff-Kishner reduction was performed. Vacuum distillation of the crude product afforded THN-olefin as a clear, colorless oil in typical yields of 98%. GC-MS analysis of the brown residue remaining in the distillation pot suggested trace amounts residual dihydrazone intermediate.

Finally, THN-olefin was hydrogenated to afford the final product (hydro-THN). Crabtree's catalyst was selected over other homogeneous hydrogenation catalysts given its excellent reactivity with hindered olefins. The reaction proceeded quickly, completing in less than an hour. GC-MS analysis of the reaction mixture revealed a slight shift in the retention time and the mass spectrum suggested that the desired product had been formed (m/z of 206, as expected, with a mass-to-charge ratio greater than the starting material by two). The reaction, however, did not go to completion, and resulted in a mixture of unsaturated and saturated in an approximate ratio of 60% to 40%. Complete conversion was afforded by treating the olefin under hydrogen pressure of higher than 50 psig in the presence of a catalyst.

Structural and Spectroscopic Characterization

Infrared spectroscopy provides a convenient method to monitor each step in the synthesis of hydro-THN. After the reaction between myrtenal and isoprene, the crystalline product, THN-aldehyde, exhibits several diagnostic peaks. The weak sharp peak at 3052 $cm^{-1}$ in the IR spectrum confirms the presences of a vinyl C—H group. The aliphatic C—H stretch at 2903 $cm^{-1}$ possessed two prominent shoulders at 2860 and 2710 $cm^{-1}$, which are indicative of the aldehyde C—H. Finally, the carbonyl C—O stretch was present at 1722 $cm^{-1}$. Upon reduction of THN-aldehyde with hydrazine, the loss of the aldehyde functional group to form THN-olefin was evidenced by a disappearance of the peaks corresponding to the C=O stretch, along with an appearance of the shoulder peaks on the aliphatic C—H stretch. Hydrogenation of THN-olefin to hydro-THN resulted in a substantially less featured IR spectrum. The major peaks were the C—H stretches centered around 2895 $cm^{-1}$ and the C—H bends at 1453 and 1367 cm-1.

To assess the purity of the products, gas chromatography mass spectrometry (GC-MS) was used. The initial Diels-Alder reaction was monitored by GC-MS. The reaction mixture was sampled at various time points for chromatographic analysis, and the results suggest that the reaction proceeds cleanly from reactants to THN-aldehyde (m/z of 218) with no major competing side reaction. This suggests that the lower than 100% yields can be attributed to losses during recrystallization. After conversion to THN-olefin and purification by distillation, the chromatograph exhibited a single peak, with the expected m/z of 204. Finally, GC-MS analysis of hydro-THN similarly shows only a single peak in the chromatograph, with the expected m/z of 206. There are some additional small peaks in the baseline of the chromatograph, suggesting the possibility of other side reactions in the hydrogenation process. Nevertheless, the desired product is by far the dominant species.

Figure 2:
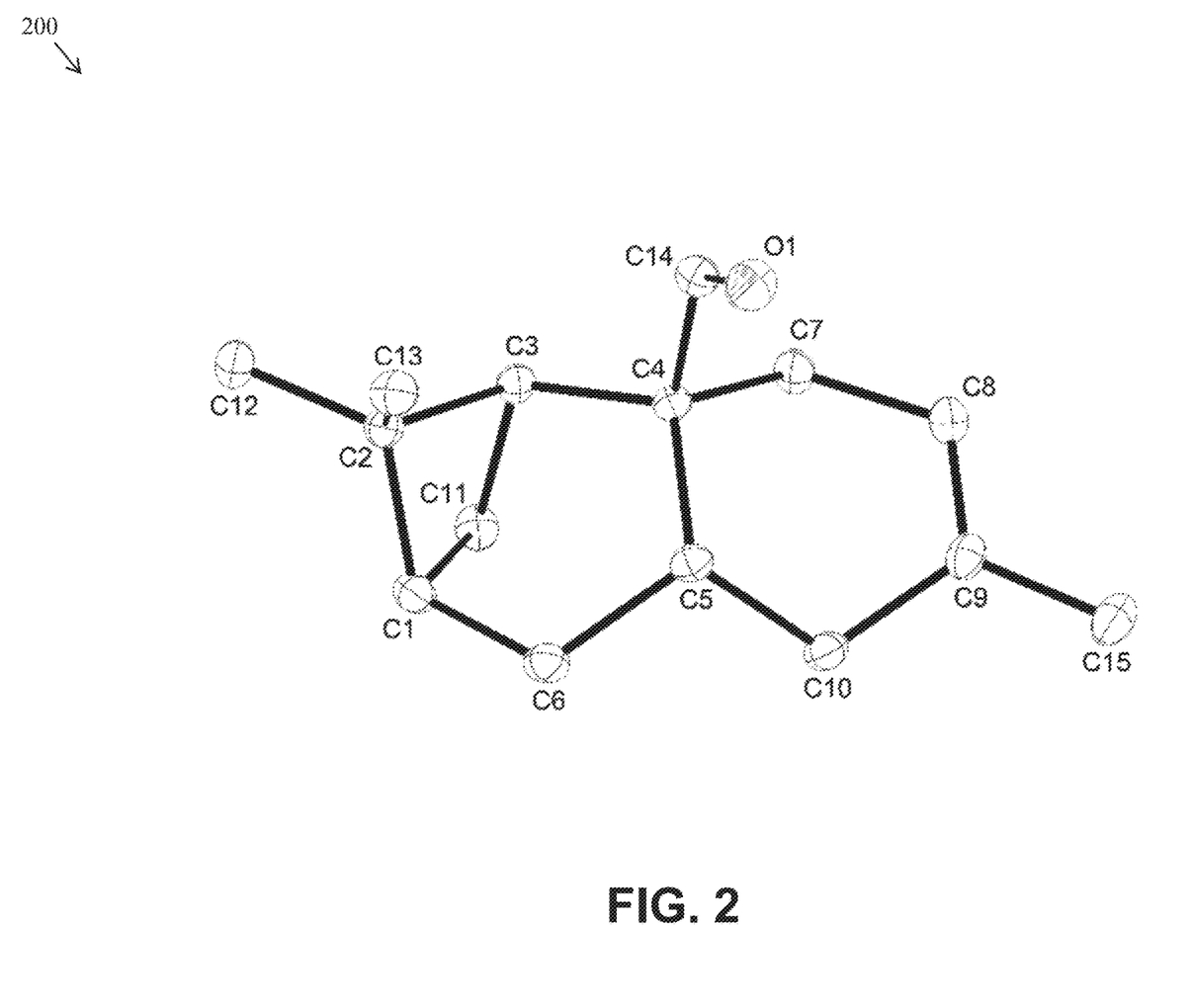
FIG. 2 is a thermal ellipsoid plot of (1S,3R,8aS)-2,2,6-trimethyl-2,3,4,4a,5,8-hexahydro-1,3-methanonaphthalene-8a (1H)-carbaldehyde (hereinafter "THN-aldehyde"), a nonlimiting example of the second intermediate molecule of the method described in FIG. 1; the probability level was set at 50%; hydrogen atoms have been omitted for clarity.

Single-crystal X-ray diffraction provides a clear picture of atomic connectivity and aids in elucidating the molecular structures reported herein (see FIG. 2, plot 200). Given the high quality of the data set, all atoms, including H-atoms, were located in the difference map and their positions were allowed to freely refine. From the obtained crystallographic data, the regioselectivity of the Diels-Alder reaction can be seen. As anticipated, the isoprene molecule approached the sterically less hindered face of myrtenal (i.e., the face lacking the gem-dimethyl bridgehead). This sets the stereochemistry of C4 and C5, arranging the aldehyde and proton on the same face as the gem-dimethyl group, respectively. The orientation of the isoprene methyl group relative to the aldehyde group is also consistent with that predicted.

Figure 3:
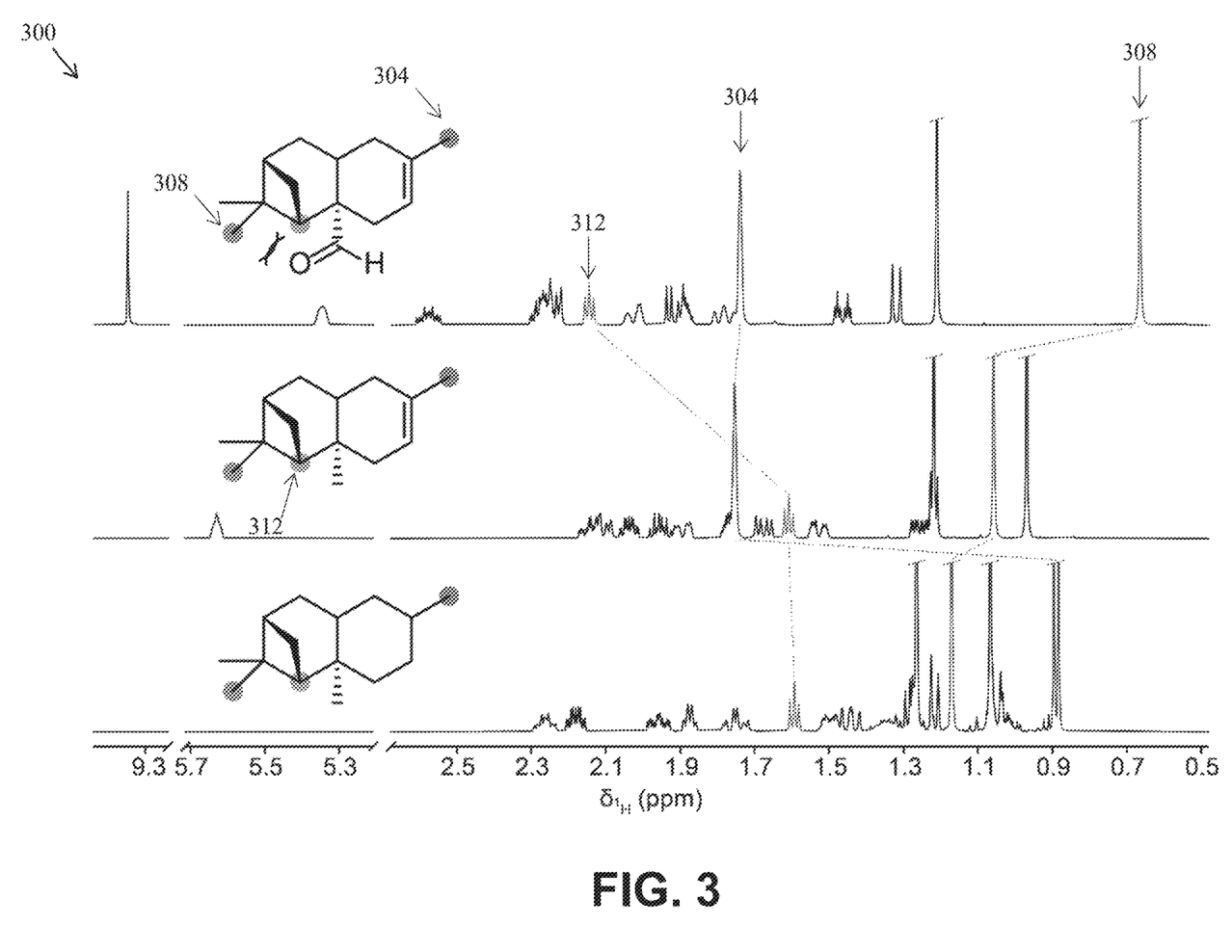
Figure 4:
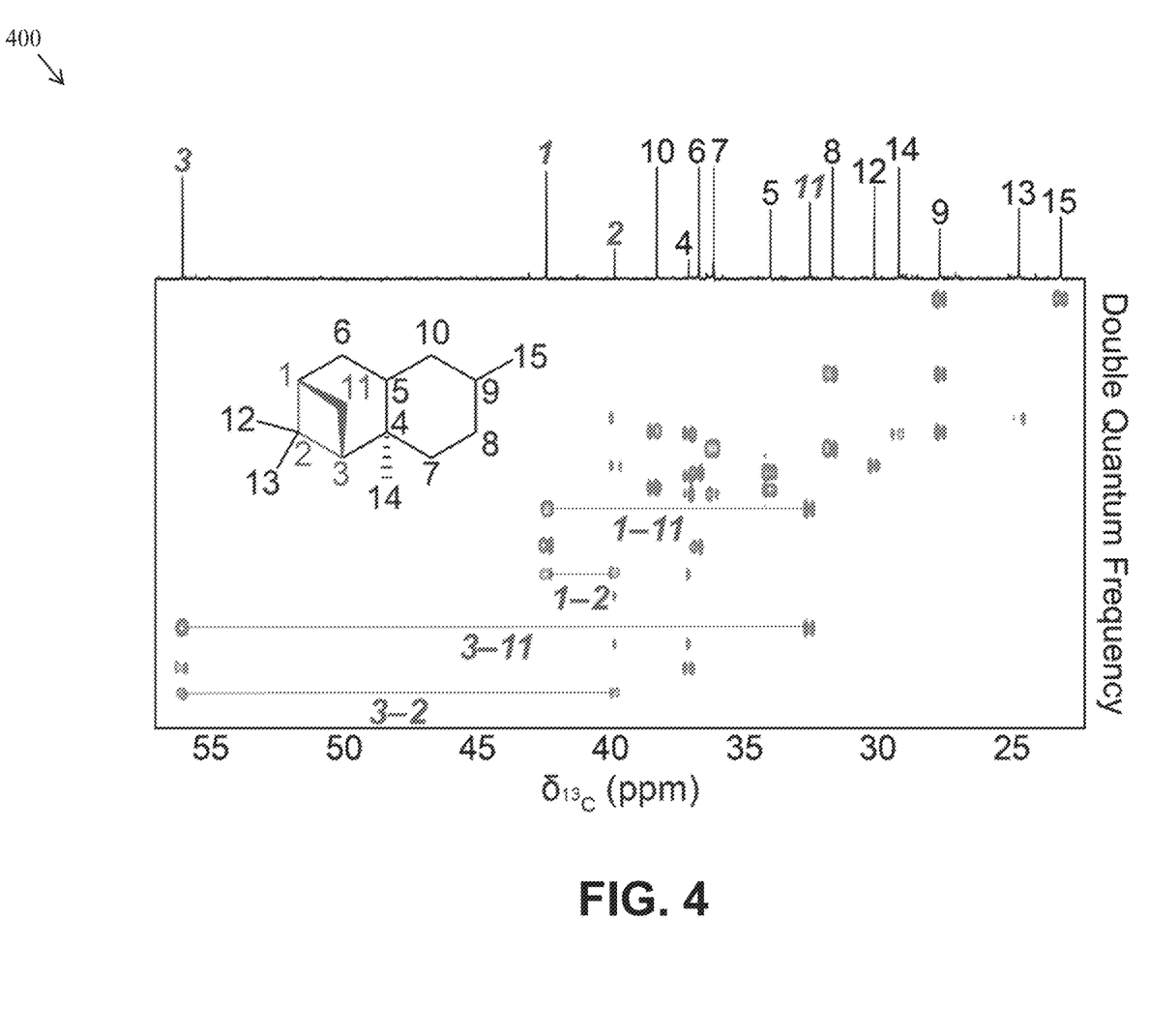
FIG. 4 is a 2D INADEQUATE spectrum of hydro-THN, a nonlimiting example of the second bicyclic compound described in FIG. 1. The highlighted correlations support an assignment of the cyclobutane ring formed by C1, C2, C3, and C11; the spectrum was acquired on a spectrometer operating at 126 MHz using neat hydro-THN mixed with 10% deuterated chloroform ($CDCl_3$).

NMR spectroscopy was used to structurally characterize the synthesized sesquiterpenes. The aldehyde and olefin functional groups provided greater diversity in chemical environments, and thus made the NMR spectra of THN-aldehyde straightforward for interpretation/assignment. The $^1$H NMR spectrum (see FIG. 3, spectra 300) contains the expected aldehyde (9.34 ppm), olefin (5.34 ppm), and methyl proton resonances (1.74, 1.21, and 0.66 ppm), along with several multiplets of varying complexity in the aliphatic region. Three groups of protons were labelled as 304, 308, and 312, respectively, to assist the assignment of peaks. The $^{13}$C {$^1$H} spectrum (see FIG. 4, spectrum 400) exhibited the expected 15 resonances. The carbonyl (206.78 ppm), and olefin carbons (139.80 and 118.24 ppm) were easily assigned based on chemical shift. Reduction of the aldehyde functionality to a methyl group was supported in the $^1$H NMR spectrum of THN-olefin by the apparent loss of the aldehyde C—H resonance, and concomitant appearance of a fourth methyl resonance. The $^{13}$C {$^1$H} spectrum further supported the conversion of the aldehyde to a methyl group with the loss of the aldehyde resonance, and appearance of a fourth methyl resonance in the aliphatic region. The two olefin carbon resonances persisted (135.38 and 123.16 ppm). The remaining carbon resonances were all grouped in the aliphatic carbon region (<50 ppm) with a single exception at 55.54 ppm, which is assigned to C3. This assignment is made on the basis that the strained cyclobutane ring leads to a substantial upfield shift. Using the 2D INADEQUATE spectrum (see FIG. 4, spectra 400), a full assignment of the $^{13}$C spectrum was made possible. Beginning with the downfield C3 resonance, the cyclobutane ring can easily be traced. Further evidence to support the integrity of the cyclobutane ring can be found in the COSY spectrum, specifically the four-bond coupling between H3 and H1. This is typical of cyclobutane rings. Hydrogenation of THN-olefin to form hydro-THN was confirmed by the loss of the olefinic $^1$H and $^{13}$C resonances. All resonances were found in the aliphatic region. Splitting of the three H15 methyl protons to a doublet further supported the hydrogenation. Ultimately, 2D INADEQUATE experiments in conjunction with HSQC, HMBC, and DQF-COSY 2D techniques allowed for a complete structural assignment.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for producing a bicyclic hydrocarbon molecule, the method comprising:
    oxidizing a terpene molecule to provide a first intermediate compound, wherein the first intermediate compound comprises an aldehyde functional group;
    reacting the first intermediate compound with a 1,3-diene molecule to form a second intermediate compound comprising the aldehyde functional group; and
    reducing the second intermediate compound to yield a first bicyclic hydrocarbon molecule, wherein reducing the second intermediate compound comprises removing the aldehyde functional group.

2. The method of claim 1, wherein the terpene molecule comprises a monoterpene molecule.

3. The method of claim 2, wherein the monoterpene molecule comprises α-pinene.

4. The method of claim 1, wherein oxidizing the terpene molecule comprises oxidizing the terpene molecule using an oxidizing agent comprising selenium dioxide ($SeO_2$).

5. The method of claim 4, wherein the oxidizing agent is dispersed in a solvent comprising ethanol (EtOH).

6. The method of claim 1, wherein the first intermediate compound comprises myrtenal ($C_{10}H_{14}O$).

7. The method of claim 1, wherein a reaction between the first intermediate compound and the 1,3-diene molecule comprises a Diels-Alder reaction.

8. The method of claim 1, wherein a reaction between the first intermediate compound and the 1,3-diene molecule is catalyzed by catalyst.

9. The method of claim 8, wherein the catalyst comprises a Lewis acid catalyst.

10. The method of claim 9, wherein the Lewis acid catalyst comprises a concentration of boron trifluoride dissolved in diethyl ether.

11. The method of claim 1, wherein the second intermediate compound has a structure of:

12. The method of claim 1, wherein reducing the second intermediate compound comprises reducing the second intermediate compound using a reducing agent comprising hydrazine monohydrate.

13. The method of claim 12, wherein the reducing agent is dispersed in an ethylene glycol solution comprising a concentration of potassium hydroxide (KOH).

14. The method of claim 1, wherein the first bicyclic hydrocarbon molecule comprises a sesquiterpene molecule.

15. The method of claim 1, wherein the first bicyclic hydrocarbon molecule comprises an unsaturated bicyclic hydrocarbon molecule.

16. The method of claim 15, wherein the unsaturated bicyclic hydrocarbon molecule has a structure of:

17. The method of claim 1, further comprising hydrogenating the first bicyclic hydrocarbon molecule to produce a second bicyclic hydrocarbon molecule.

18. The method of claim 17, wherein the second bicyclic hydrocarbon molecule has a structure of:

* * * * *